United States Patent [19]

Toftness

[11] Patent Number: 4,479,498

[45] Date of Patent: Oct. 30, 1984

[54] METHOD OF SPINAL RADIOMETER ANALYSIS AND CORRECTIVE ADJUSTMENT

[76] Inventor: Irwing N. Toftness, 1425 Second Ave., Cumberland, Wis. 54829

[21] Appl. No.: 412,158

[22] Filed: Aug. 27, 1982

[51] Int. Cl.$^3$ .............................................. A61B 6/00
[52] U.S. Cl. .................................... 128/653; 128/736
[58] Field of Search ............................... 128/736, 653

[56] References Cited

U.S. PATENT DOCUMENTS 4,275,741  6/1981  Edrich ............................ 128/736 X
4,347,854  9/1982  Gosline et al. ....................... 128/736

OTHER PUBLICATIONS

Barrett, A. H. et al., "Subcutaneous Temperatures: A Method of Non-Invasive Sensing", Science, V190, 11/14/75.

Primary Examiner—Kyle L. Howell
Assistant Examiner—Francis J. Jaworski
Attorney, Agent, or Firm—Leo Gregory

[57] ABSTRACT

The method of analysis and corrective adjustment of a human body including scanning the body, and particularly the spinal column area, by an appropriately tuned radiometer to collect and display measured microwave emissions for detection of areas of stress such as may be present in connective tissue, nerve tissue or muscular tissue, the scanning permitting an analysis of subcutaneous microwave emissions from depths up to several centimeters, converting the collected emissions into a visual measured output, comparing the resulting output to a reference representing a normal range of emissions and observing during the application of corrective adjustment, the extent of correction being provided as changes displayed in the collected emissions are compared with the reference of a normal condition and noting through the application of corrective adjustment pressure in several radial directions, the particular radial direction in which the application of pressure secures the maximum reduction in deviation from said normal reference.

7 Claims, 2 Drawing Figures

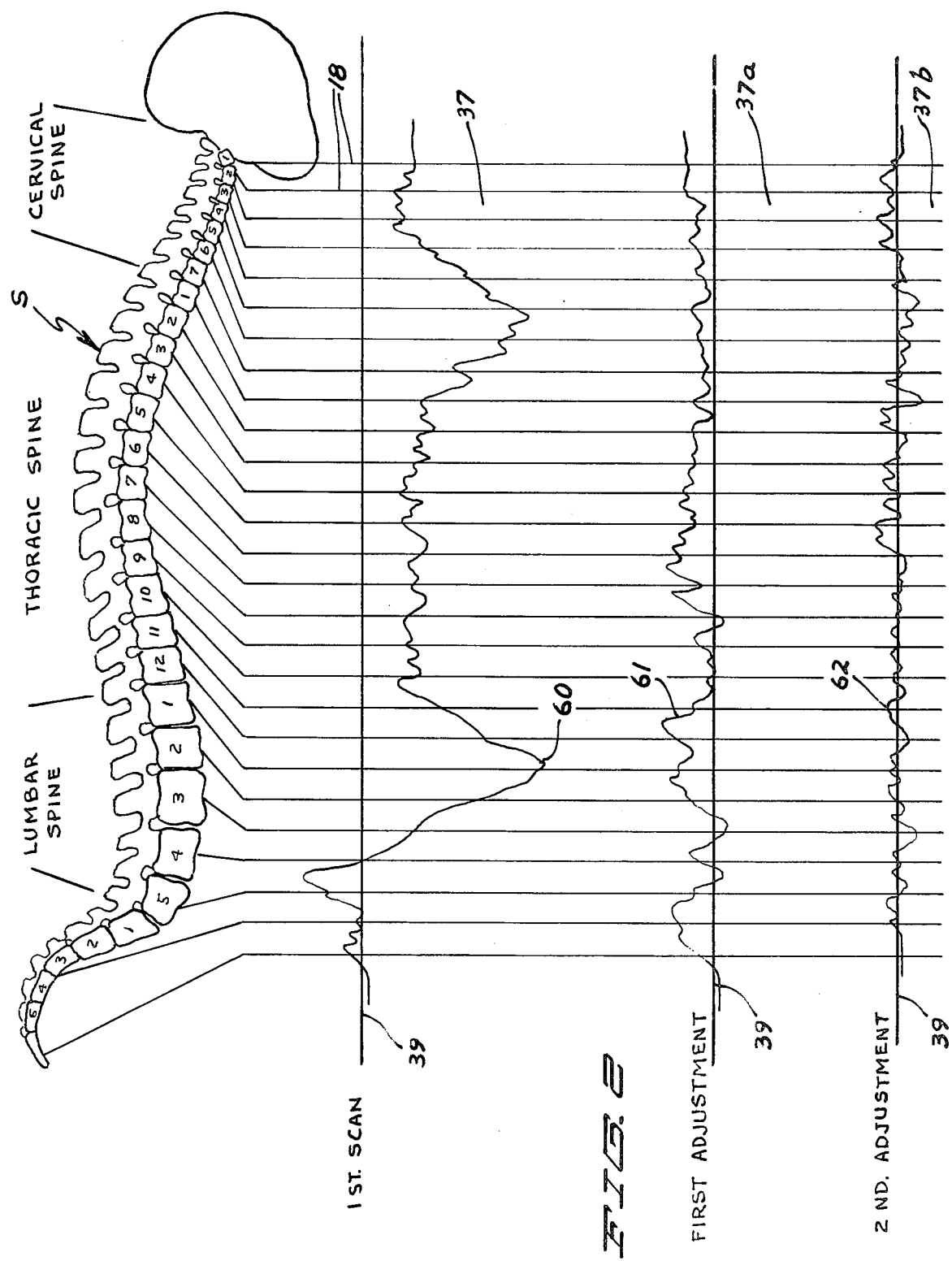

METHOD OF SPINAL RADIOMETER ANALYSIS AND CORRECTIVE ADJUSTMENT

BACKGROUND OF THE INVENTION

1. Field of the Invention

This invention relates to a method of applying a technique which represents an improvement in the corrective adjustment applied to a human body with regard to stress areas as in the spinal column area and the application of such technique with the assistance of a display of the collection and measurement of microwave emissions in the area of adjustment.

2. Description of the Prior Art

The analysis in the spinal column area of a body for detection of stress conditions has been traditionally an analysis based upon palpation and X-ray imaging. Such analysis does not detect small structural changes which may cause acute and chronic pathologic conditions and does not disclose non-structural effects. In connection with X-ray imaging, there is present the attendant radiation hazard. Infrared thermography is also utilized but does not provide sufficiently adequate information for corrective adjustment purposes.

With reference to U.S. Pat. No. 4,034,234, a disclosure is made of an effort to utilize skin temperature indications by means of a thermally active crystal sheet laid over the body of a patient for an indication by a display of color of areas of trauma. An overhead camera is used to reduce the color appearance of the crystal sheet to a photographic print. Here the emphasis is upon combining a color indication of temperature with palpation to ascertain areas requiring correction. The emphasis here is also upon photographing the appearance of skin temperature as evidenced by a thermal sheet as a guide in connection with conventional corrective adjustment. There is no indication here of collecting and measuring subcutaneous microwave emissions from a body to indicate specific points of stress.

In U.S. Pat. No. 3,374,354, an infrared scanning device is shown to scan surface or skin temperatures through a slot in a table under which the patient is positioned and observed. The application of infrared thermography might substitute for the crystal sheet of the above U.S. Pat. No. 4,034,324, were a teaching present to adapt the apparatus used in infrared thermography in such a manner that the patient's body could be acted upon for chiropractic adjustment at the time that the scan readings are taken.

The invention herein discloses improvement in the technique of corrective adjustment and in connection therewith it discloses and provides a significant improvement in analysis by collecting and displaying measured subcutaneous microwave emissions from the body and such measured emissions indicate specific stress areas, and provide significant analysis information which neither the use of a crystal sheet nor infrared thermography are capable of providing.

SUMMARY OF THE INVENTION

The human body emits electromagnetic or microwave radiation and reacts to areas of stress by emitting intensified radiation from the affected areas such as in connective tissue, nerve tissue, or muscular tissue. The intensity of radiation detected can be measured in mm (millimeter) wavelengths and can be picked up by a suitable electronic receiver such as a Dicke radiometer tuned to receive a specific frequency for measuring and indicating on a strip chart a readout or a visual analog display of microwave levels or intensity of radiation emitted and the changes occurring therein. The spinal column area is particularly well suited for radiation detection because it contains largely material with low electrical loss such as bone which provides very little impedance and the mm wavelength detection may originate from relatively deep subcutaneous abnormalities.

The invention herein relates to a substantial improvement in the art of collecting and measuring body radiation for the purpose of indicating the presence of stress, the collected radiation is converted immediately into a visual measured display which shows the nature of the corresponding normal condition and further indicates during the course of corrective adjustment the improvement resulting from the adjustment by a constant and continuing comparison being made of microwave emissions from the adjusted areas compared with a normal reference of such emissions.

More particularly, the invention herein relates to a method of analysis including collecting, measuring and visually observing by mm wave or microwave emissions from a spinal column area or other parts of a human body to determine the presence of areas of stress or nerve interference in connection with the application of a particular technique of corrective adjustment to relieve the stress areas.

It is an object of the invention herein to provide a method of corrective adjustment of the body of a patient in association with a radiometer providing a mm wavelength detection to indicate by a visual display the extent, if any, to which the radiation collected along the spinal column deviates from a corresponding reference indication of a normal condition of emission of radiation and thus by noting the specific points of deviation of the sensed radiation from the corresponding reference, the particular areas of stress are detected with pinpoint accuracy to indicate where corrective adjustment is to be made, the area of adjustment is scanned by the radiometer during the course of adjustment and the display indicates substantially simultaneously with the adjustment being made the effect of such adjustment and the relief from nerve interference by a continuous comparison of the emitted radiation with the reference indicating a normal condition.

More specifically, this invention of corrective adjustment embodies the collection and measurement of microwave emissions from the body, said emissions being collected in a frequency selected from a range such as on the order of 9.85 to 69.5 gHz, the selected frequency being relatively free from interference and converting said frequency received into a signal to display the same such as a graph line on a strip chart or an analog reading on a meter dial, such display including a comparison to a corresponding reference indicating a normal condition of body emissions.

These and other objects and advantages of the invention will be set forth in the following description made in connection with the accompanying drawings in which like reference characters refer to similar parts throughout the several views.

BRIEF DESCRIPTION OF THE DRAWINGS

FIG. 1 is a view in side elevation showing the apparatus in operating position.

DESCRIPTION OF A PREFERRED EMBODIMENT

Figure 2:
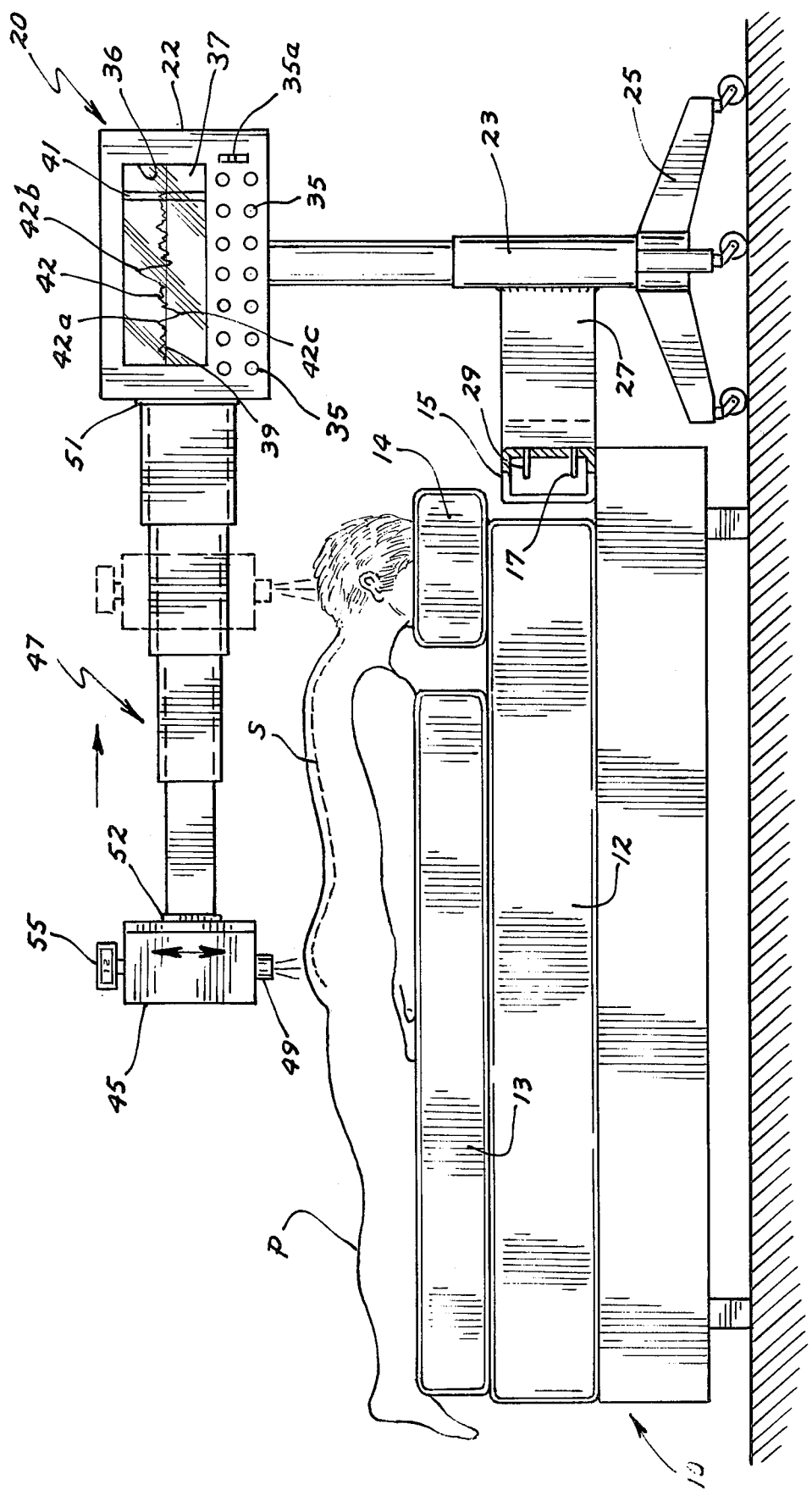
FIG. 2 is a view showing a comparison of three chart readings in relation to a skeletal view of a spinal column.

The method herein represents in combination improvement in the technique of making an analysis of the human body with particular reference to the spinal column area to ascertain the presence of and pinpoint the location of distress areas or areas of nerve interference and improvement in the technique of applying corrective adjustment.

The human body emits electromagnetic or microwave radiation. The emissions indicate that thermal radiation is generated internally and relates to internal temperature. Because of the electromagnetic properties of biological tissue, radiation at a microwave frequency can be collected from a depth in the human body of several centimeters. Thus internal radiation is measured and read in a very precise manner.

This collection of body radiation is not to be related to infrared thermography which for all practical purposes detects only surface temperatures which may not provide precise and sufficiently meaningful information.

The output reading of the radiation collected in the method herein will be proportional to the internal temperature of the body in the areas scanned and thus the apparatus herein serves as a remote temperature sensor.

The apparatus indicated herein to carry out the method of corrective adjustment in combination with the detection of radiation includes a radiometer such as a Dicke radiometer tuned in for purposes herein to 17 gHz at which level scanning may be made to be relatively fast and an integration time such as on the order from 0.3 seconds and extending to one or two seconds may be desired for the time interval of conversion from the collection of radiation to its reproduction as a visible display. This may be made to be a graph line on a strip chart or an analog reading on a meter dial or both simultaneously.

APPARATUS USED

With reference to FIG. 1, there is shown a conventional patient examination table 10 suitably formed and embodying the mechanism and controls for height adjustment and consisting of a supporting base 12, a body mat 13 and a head rest 14.

Shown in operative association with said table is a radiometer 20 of conventional state of the art structure comprising a console 22 mounted onto a vertically adjustable post or column 23 and supported by a mobile base 25.

Carried at the head of said examination table is a keeper or locking member 15 to which said radiometer is suitably removably secured by a magnetic latching member 27 which has a pair of projecting mating pins 29 which are received into corresponding holes 17 of said locking member 15. Thus, there is provided an attachment for alignment of the radiometer with the examination table.

Carried on the console of said radiometer are the operating controls or switches 35 which will be labeled and will actuate the various functions of the radiometer, all of which is conventional in the art. The operation of the radiometer will be described without reference to specific controls.

The face 36 of said console will receive a sheet of strip chart paper or strip chart 37 underlying the recorder 41 which will travel across the chart. Appearing on said chart is a line 42 representing the radiation or emissions collected in a spinal column scan. The line 39 on said chart represents a reference line indicating a normal pattern of emissions for comparison purposes. As used herein, the words radiation and emissions are interchangeable and both refer to microwave emissions.

A telescopic arm or bracket 47 is carried attached to said console 22 as at 51 and has mounted at its free end as at 52 a sensing or scanning head 45. The mounting of said head at 52 will be such as to provide vertical adjustment of said head for purpose of scanning. The electronic connection between said head and said console is conventional as is the entire operation of the radiometer.

Said bracket as presented here will be extended manually and retracted by a timed motor drive which in a coordinated effort causes the recorder to travel across the chart in the same interval of time that the sensing head will be moved to scan the length of the spinal column. Thus every point in the line drawn upon the chart relates to and represents a corresponding specific point in the spinal column area as indicated in FIG. 2.

Said sensing head or member 45 is shown including a horn 49 to collect the radiation scanned. Included in the sensing head and in the body of the console are the conventional components to convert the radiation collected into a signal which is displayed as line 42 on the strip chart and which may be otherwise displayed as by the analog meter 55 which is carried by the sensing head. Thus two readings of microwave emissions are conveniently at hand. The analog reading will have a zero reading as a normal condition for reference purposes and the chart line 42 will have the reference line 39 for comparison with a normal condition. The analog reading will be of the specific area of the spinal column upon which the sensing head is focused.

The radiometer usable herein is capable of being tuned to receive a selected frequency in the range of 15 to 69.5 gHz and has the capability of a fast integration time as on the order of 0.3 seconds, or up to one to two seconds, as desired, for conversion of sensed radiation to a visible readout. This rapid conversion time is important in the improvement of technique herein of making appropriate corrective adjustment as will be described.

The radiation emitted by the body embodies a wide range of frequencies. The selection of any given frequency does not indicate that it is a particular significant frequency with regard to body radiation but more to the point, a frequency is selected which will result in the least amount of interference in being collected and converted by the radiometer into an output to have the output represent as closely as possible, the emissions collected from the body.

Embodied within the scope of this invention though not herein shown, is the use of a computer in circuit with said radiometer to instantly reduce the display of microwave emissions, such as a graph line, to a printed reproduction and also storing the same in memory, the computer being programmed to eliminate the effects of atmospheric interference and the interference generated by the operation of the radiometer.

THE METHOD

In utilizing the apparatus indicated herein to carry out the method which comprises the invention herein, a patient will be placed face down in a prone position upon the pad 13 and head rest 14 as shown. The radiometer will be placed in operating position secured to the member 15.

In practicing the improvement in the technique of corrective adjustment as herein disclosed, a body scan is first taken to determine the general condition of the body with regard to stress or the presence of nerve interference therein by comparison of the scan taken with the reference 39 which is intended to indicate a normal condition of body emissions.

The radiometer will be energized by the switch 35a, the bracket 47 will be extended to position the sensing head 45 as above the sacral region preferably at a height thereabove on the order of four inches. The desired integration time will be set, such as at 0.3 seconds or at one or two seconds, whichever may be desired. The recorder 41 will traverse the strip chart coordinate with the sensing head traversing the patient's spinal column S. The bracket 47 which carries the sensing head will be retracted by a timed motor not shown which is coordinate with the movement of the chart recorder.

At the integration time indicated, radiation is collected and charted from very small discrete increments of the spinal column. Thus, there is very specific definition of the body emission collected represented by the chart scan line 42.

When the scan line 42 of the entire spinal column has been recorded on the strip chart, a general observation will be made to determine the principal stress areas (42a, 42b and 42c) by the degree of deviation of the peaks or spikes in the line of microwave radiation collected compared to the reading of the reference line 39 on the chart. The analysis thus made augments an initial or prior analysis made in accordance with conventional practice as by palpation.

The corrective adjustment to relieve nerve interference which is referred to as stress will first be applied to the point of the spinal column S which corresponds to the point of greatest stress or deviation from the reference line as indicated by the spike (42b). The strip chart is ruled in squares to give a convenient centimeter measurement of deviation.

At the commencement of the adjustment, the horn 49 will be positioned to focus upon said spinal column area where corrective adjustment will be applied first and will be held focused upon such area to indicate the effect of the adjustment.

In general conventional practice, pressure is applied to relieve a subluxation in no particular predetermined direction and can be stated as being applied in a downward direction upon a prone body or in other words, inwardly of the body.

The method of adjustment herein described represents a significant improvement in the art of corrective adjustment. To correct a subluxation in a spinal column in a conventional manner requires the displacement or the abrupt physical movement of a vertebrae to restore or move it sufficiently to its proper or natural position to relieve distressing pressure. This is a sudden application of substantial force.

It has been found that more effective results are secured not by a sudden forceful application of pressure but by a steady application of relatively light pressure of only three to four ounces sustained for the period of time required to restore a displaced vertebrae to its natural position to the extent that the body will sustain the correction.

The critical aspect of the method of adjustment herein is that pressure be applied at the appropriate place in a precise line of direction. Pressure is applied with a thumb or forefinger as an oblique pointer. The application of a steady pressure in a specific line of direction for a suitable time period is a salient distinguishing element.

With the sensing head 45 focused upon the area of adjustment and with the fast integration time indicated, pressure will first be applied at the selected point of the spinal column in various radial directions while observing the recording strip chart and for the analog reading. The appropriate line of direction for application of pressure will be the one in which the deviation of the readout is reduced the most in comparison with a normal reference reading. Thus there is indicated the specific direction of the application of pressure in which the distressed area is given maximum relief or maximum correction. The pressure will be applied steadily until such time that when the nerve interference is relieved, the strip chart or analog reading indicate that the relief from stress is sustained by the body.

Next, reference is had to the initial strip chart reading of the entire spinal column area and the area of the next greatest deviation will be attended to. The sensing head 45 will be focused upon this area, the extent of deviation will be observed and pressure will be applied in various radial directions to determine the direction of line of drive of the applied pressure in which the deviation is brought into closest correspondence with the normal reference, pressure will be applied in this direction until the stress or nerve interference is overcome to the extent it can be sustained by the body. Thus the adjustment will be continued until all of the stressed areas indicated have been corrected.

The specific degree of correction to each point of stress is readily ascertained by observing the readout of the stressed condition. Frequently relief at a major point of stress may result in relief at one or more minor points of stress.

A point of stress in the body may shift whereby during the application of corrective adjusting pressure another line of direction of applied pressure may be more effective. This is readily ascertained by the pivotal movement of the finger about the point at which pressure is applied while observing the effect of the change of direction upon the radiation emitted as evidenced by the recording upon the strip chart or by observing the analog reading.

When corrective adjustment has been completed, the entire spinal column will be scanned to show the effect of the adjustment made compared both to the initial scan 42 taken and to the normal reference lines 39. It will be understood that corrective adjustment although generally applied to regions of the spinal column may be made elsewhere on the body as required.

There may be points of stress in osseous articulations of the body and these will be determined in the same manner as scanning the spine and pressure will be applied in an appropriate line of direction to relieve the stress.

Referring to FIG. 2, the normal condition reference line 39 is shown and compared therewith are line 60 representing an initial scan, the line 61 showing a scan taken following a first corrective adjustment and the line 62 showing the effect of a second corrective adjustment.

To conserve space, the charts 17, 17a and 17b of FIG. 2 are partially broken away and superposed. The chart lines 18 make direct reference to specific spinal column locations.

Very precise reference is had in correlating what is shown and read on a chart with a corresponding point in the spinal column.

The scan lines 61 and 62 show a progressive closer correspondence with the normal reference line 39 compared to the initial scan shown by line 60.

The very significant success experienced results from two basic factors, namely, having precise reliable information as to the stress conditions in the body, such information resulting from collecting and reading microwave emissions having subcutaneous origins of substantial depth, by relating such information to specific points of stress in the spinal column which are indicated and located directly by the scan lines and by having this information on an ongoing basis all during the course of making corrective adjustment with said information giving guidance to the making of the corrective adjustment. This information permits a precise application of the adjustment technique herein decribed.

It will be understood that corrective adjustment although generally applied to the spinal column area, may be applied elsewhere upon the body wherever stress conditions are indicated and the body may be in a sitting or in an upright position.

The technique of corrective adjustment herein described for all of its simplicity is a significant development and has been developed through extensive research effort with remarkably successful results in connection with the use of mm microwave detection and collection as described herein which gives a direct almost instantaneous visual observation of the ongoing results being achieved during the application of the corrective adjustment. No reliance is required to be placed upon subjective information from the patient as to how the patient feels nor upon tactile sensitivity in sensing by palpation. Instead, there is provided a direct visual electronic created reading which may be compared to a prior reference of the condition of the body and which may be compared to a normal condition reference and ongoing effects are observed. Further, for historical purposes, there is provided a very detailed analytic comparison between one treatment and the next.

It will of course be understood that various changes may be made in form, details, arrangement and proportions of the parts without departing from the scope of the invention herein which, generally stated, consists in an apparatus capable of carrying out the objects above set forth, in the parts and combinations of parts disclosed and defined in the appended claims.

What is claimed is:

1. The method of analysis and corrective adjustment for relief of nerve interference in the human body, consisting of the steps of
    positioning the body of the patient,
    scanning subcutaneous microwave emissions from the spinal column area of the patient,
    collecting and converting said emissions into a measured visual output representing a pattern of the intensity of emissions of the spinal column,
    providing a visual reference of a normal pattern of said emissions for comparison with said output of said spinal column,
    observing the deviations of said output compared with said normal pattern of emissions, said deviations representing microwave emissions which pinpoint stress areas,
    applying corrective adjustment to said spinal column to the portions thereof corresponding to the points of said deviations, said corrective adjustment consisting of placing oblique thumb or finger pressure upon a point of the spinal column corresponding with a point of deviation of said emissions,
    collecting and converting into a visual measured output the microwave emissions at said point of applied pressure,
    pivoting said thumb or finger upon said point to apply said pressure in various radial directions,
    observing the visual output of microwave emissions at each radial direction of application of pressure,
    noting the line of direction of the application of said pressure in which is achieved the maximum reduction of deviation of microwave emissions compared to said normal reference of emissions,
    continuing the application of pressure in said last mentioned line of direction until the reduction in microwave emissions is sustained,
    repeating the steps of ascertaining and applying pressure in the radial line of direction to achieve a maximum reduction of deviation in microwave emissions at each point of deviation of emissions from said normal reference of emissions, and
    scanning said spinal column at the completion of adjustment comparing the visual output of emissions to said normal reference of emissions to determine the effect of the corrective adjustment.

2. The method of analysis and relief of nerve interference in the human body, consisting of the steps of
    positioning the body of the patient,
    scanning the microwave emissions from the spinal column of the patient,
    collecting and converting said emissions scanned into a measured visual output of the intensity of emissions from the spinal column,
    providing a normal reference for comparison with said output of emissions,
    observing points of deviation of said output from said normal reference, said points of deviation pinpointing areas of stess,
    applying corrective adjustment at each of said points of deviation, said corrective adjustment at each of said points of stress consisting of applying an oblique thumb or finger pressure upon a point of the spinal column corresponding with a point of said deviation,
    pivoting said thumb or finger pressure in various radial lines of direction about said point of deviation,
    collecting and converting into a measured visual output, the emissions at said point of pressure in each of said radial lines of direction,
    comparing said output of emissions at said point of pressure in each of said radial directions to said normal reference and said first visual output of emissions,
    continuing said pressure in the radial line of direction in which is seen to occur the greatest reduction in deviation from said normal reference, continuing the application of pressure in said last mentioned line of direction until said emission approximates at a corresponding point that of said normal reference as closely as is judged possible in view of the patient's condition, and scanning said spinal column subsequent to said application of corrective adjustment to the points of deviation to compare the output of emissions therefrom with said normal reference to ascertain the resulting effect from the corrective adjustment made.

3. The method of analysis and adjustment of stress areas relieving nerve interference in the human body, consisting of the steps of positioning the body of the patient, scanning the microwave emissions from the spinal column area of the patient, collecting and converting said scanned emissions into a measured visual line output, comparing said line output with a reference indicating a normal condition of subcutaneous microwave emissions from a spinal column of a human body, observing the points of deviation of said scanned output from said reference, said points of deviation pinpointing areas of stress, applying corrective adjustment to said points of deviation, said corrective adjustment consisting of applying an oblique thumb or finger pressure upon each point of the spinal column corresponding with a point of said deviation, pivoting said thumb or finger pressure in various radial lines of direction about each said point, collecting and converting into a visual reading the output of the emissions at each said point of pressure for each radial line of direction of the application of said pressure, observing said output at each of said radial lines of direction of applied pressure to ascertain the line of direction in which the deviation shows the greatest reduction of deviation from said normal reference, applying said pressure in said last mentioned line of direction, continuing the application of said pressure in said last mentioned line of direction until the microwave emission at said point approximates said normal reference as closely as is judged possible, and scanning said spinal column subsequent to said application of corrective adjustment to compare the pattern of emission output therefrom with said normal reference to indicate the result of said corrective adjustments with respect to the entire spinal column area.

4. The steps set forth in claims 1, 2 or 3, including providing said normal reference as a line on a strip chart, recording said measured output as a line on said strip chart, and providing indicia on said strip chart measuring the comparison between said normal reference and said output line.

5. The steps set forth in claims 1, 2 or 3, including providing an analog reading of said visual output, and noting deviations of said analog reading of microwave emissions collected compared to a normal reference condition of zero.

6. The steps set forth in claims 1, 2 or 3, including scanning and collecting said microwave emissions with an appropriately tuned radiometer, providing said radiometer with a strip chart, including a normal reference line on said strip chart, and providing indicia on said strip chart for a measured comparison of collected emissions with said normal reference.

7. The steps set forth in claims 1, 2 or 3, including providing an appropriately tuned radiometer, embodying said radiometer with a strip chart, placing an analog meter in circuit with said radiometer, having said radiometer display said visual output on said strip chart on said analog meter, and providing said displays with comparison to a normal reference.

* * * * *